Figure 1:
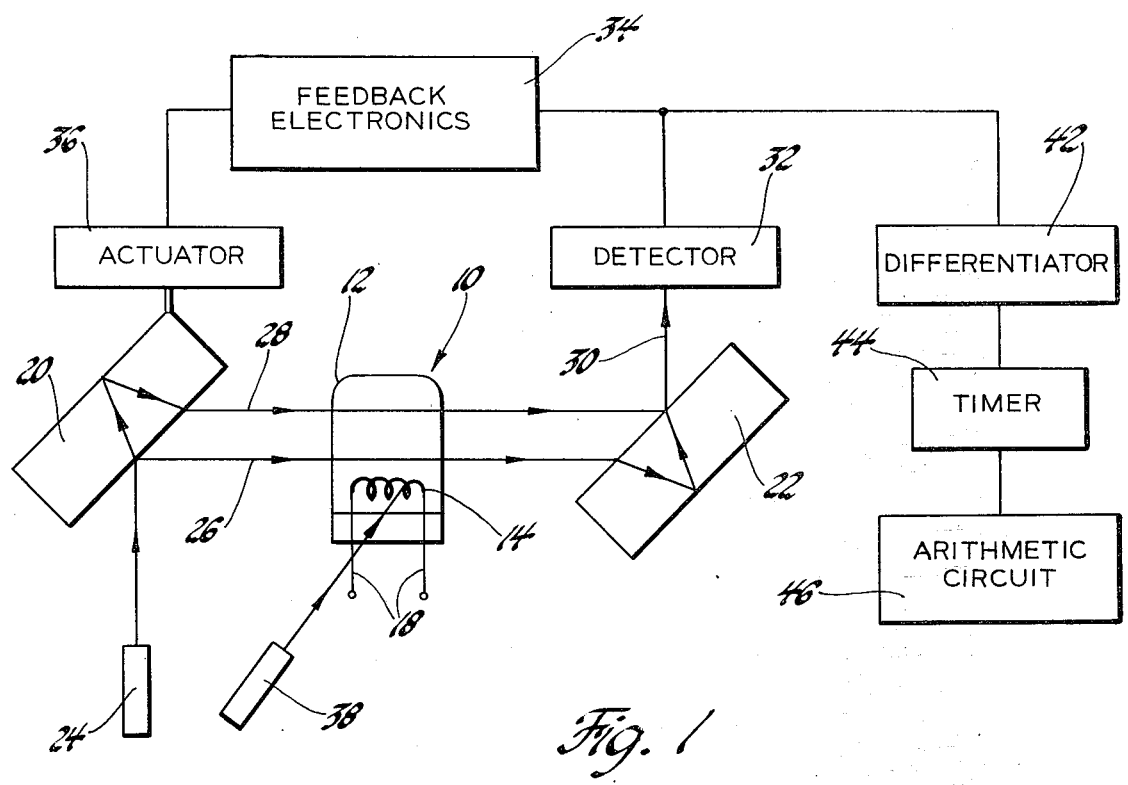

United States Patent [19]

Eesley et al.

[11] 4,452,071
[45] Jun. 5, 1984

[54] MEASUREMENT OF FILL GAS PRESSURE IN LIGHT BULBS

[75] Inventors: Gary L. Eesley, Lake Orion; Jeffrey C. Buchholz, Detroit; Jeffery A. Sell, Huntington Wood, all of Mich.

[73] Assignee: General Motors Corporation, Detroit, Mich.

[21] Appl. No.: 443,198

[22] Filed: Nov. 22, 1982

[51] Int. Cl.³ .................. G01N 29/00; G01M 3/02
[52] U.S. Cl. .............................. 73/52; 73/49.3; 73/705; 356/361
[58] Field of Search .................. 73/49.3, 52, 705, 700; 356/361

[56] References Cited

U.S. PATENT DOCUMENTS

| | | | |
|---|---|---|---|
| 3,888,111 | 6/1975 | Craig | 73/49.3 |
| 4,003,242 | 1/1977 | Houben et al. | 73/24 |
| 4,187,718 | 2/1980 | Shibasaki | 73/52 |

*Primary Examiner*—Donald O. Woodiel
*Attorney, Agent, or Firm*—Warren D. Hill

[57] ABSTRACT

Tungsten halogen lamps require a fill pressure of several atmospheres. To verify the fill pressure at the time of manufacture the pressure is indirectly measured by first measuring the speed of sound within the lamp. A shock wave is produced within the lamp by rapidly heating a lamp filament or producing an arc between two adjacent filaments and measuring the time required for the shock wave to sequentially disturb two spaced light beams passing through the lamp. The speed of sound is determined from the measured time and the pressure is calculated from the speed of sound.

3 Claims, 3 Drawing Figures

MEASUREMENT OF FILL GAS PRESSURE IN LIGHT BULBS

This invention relates to measuring the gas fill pressure in a lamp and more particularly to such a method using a measurement of the speed of sound within the lamp.

Tungsten halogen lamps which are used for automotive vehicle headlights are constructed of tungsten filaments encased in a glass envelope filled with a gas about seven atmospheres pressure, the gas comprising krypton with small amounts of a halogen. To obtain the desired efficiency and long life of the lamps the fill pressure must be near the prescribed value. Thus it is desirable to make a measurement of the fill pressure at the time of lamp manufacture to cull out improperly filled lamps and to monitor the gas fill procedures.

It is therefore an object of this invention to measure the pressure of a gas within a sealed lamp or bulb.

The invention is carried out by generating a shock wave in the bulb whereupon the speed of the shock wave depends on the gas pressure, detecting the passage of the shock wave through two spaced regions in the bulb, measuring the time of travel of the shock waves between the two regions and determining from the resulting speed measurement the fill gas pressure of the bulb.

Figure 2:
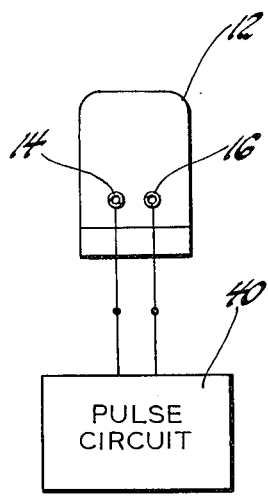
Figure 3:
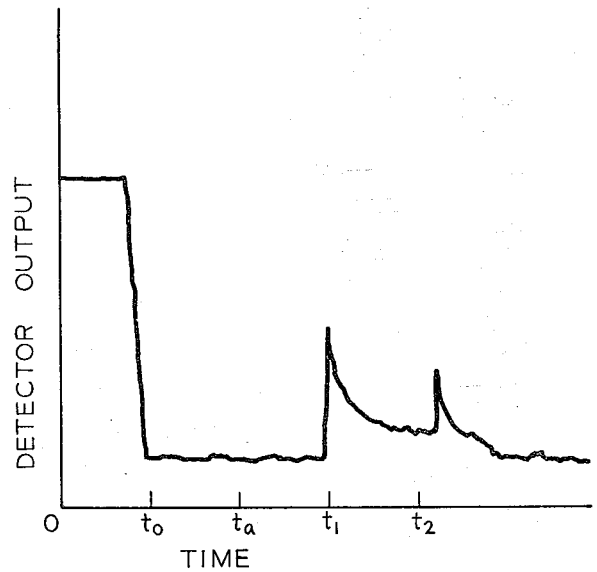

The above and other advantages will become more apparent from the following description taken in conjunction with the accompanying drawings wherein like reference numerals refer to like parts and wherein:

FIG. 1 is a diagrammatic view of a system for measuring fill gas pressure in a light bulb according to the method of the invention, FIG. 2 is a view of a bulb coupled to a pulse circuit, and FIG. 3 is a graph of electrical signals generated by the system of FIG. 1.

Referring to FIG. 1, a lamp 10 of the tungsten halogen variety has a glass envelope 12 containing a tungsten filament 14. Alternatively, as shown in FIG. 2, the envelope may contain a pair of tungsten filaments 14 and 16. Lamp leads 18 from the filaments extend through the lamp base. The envelope also contains a gas, preferably krypton, including a small concentration of a halogen at a pressure of seven atmospheres. Optical instrumentation for the pressure measurement is based on the Jamin interferometer. Mirrors 20 and 22 have fully reflecting rear surfaces and partially reflecting front coatings. A laser light source 24 projects a light beam onto the mirror 20 which reflects two parallel light beams 26 and 28 from the front and rear mirror surface respectively, the beams being of nearly equal intensity. The beams are passed through the lamp envelope 12 in two paths. The distances of the paths from the filament differs by a known amount, preferably one centimeter. The beams are recombined by the mirror 22 into a final beam 30 which impinges on a photoelectric detector 32. The detector output is a signal proportional to the intensity of the light beam 30. The signal is fed to feed back electronics 34 which are effective through an actuator 36 to slightly tilt the mirror 20 such that the beams 26 and 28 are 180° out of phase and the two beams interfere destructively to null the output signal. This nulling procedure and apparatus are well known with respect to the Jamin interferometer.

A thermal shock wave or pressure wave is generated in the lamp by rapidly heating the filament 14. For example, this might be done by applying a high voltage pulse across the filament or by focusing an external light pulse such as from a laser 38 onto the filament. In the case of the two filament lamp of FIG. 2, a preferred technique for generating a shock wave is to apply a short high voltage pulse across the filaments 14 and 16 by a pulse circuit 40 to produce a rapid electrical arc between the filaments. When the filaments are spaced by about 1 mm at their closest point, a pulse of 3200 volts is adequate to cause an arc. The shock wave so produced traverses the lamp at the speed of sound which is determined by the fill gas pressure. As the shock wave passes the path of the light beam 26 the disturbance of the light beam will produce a phase shift relative to the light beam 28 thereby producing a rapid increase in the light intensity of the beam 30 and in the detector output signal. Similarly, when the shock wave passes through the light beam 28 a second change in the output intensity and the detector signal will occur. The time period between these two signals is a measure of the speed of sound at the fill gas pressure. Circuitry coupled to the detector for utilizing this information comprises a differentiator 42 for enhancing the resolution of the signal pulses and a timer 44 responsive to the pulses to measure the time elapsed between the pulses. An arithmetic circuit 46 calculates the fill gas pressure from the measured time lapse.

FIG. 3 shows the detector output signal produced during a typical measurement cycle. At time zero when the lamp is initially placed in the path of the light beams a large signal may occur and then the feed back electronics 34 and the actuator 36 effect adjustment of the mirror 20 to null the signal thereupon bringing it to a low value at $t_0$. At time $t_a$ a shock wave is generated at the filament by the laser 38 or the pulse circuit 40. At time $t_1$ the shock wave passes through the beam 26 momentarily changing the phase of the light beam and causing a large peak in the signal and at times $t_2$ the shock wave passes through the beam 28 to cause another peak in the signal. Since the light beams are at a fixed spacing in the direction of the shock wave propagation the period between the times $t_1$ and $t_2$ is a function of the speed of sound in the gas.

To the first order of approximation the speed of sound in gas is considered to be independent of pressure. However, careful measurements reveal a minor influence of pressure on the speed of sound. Such measurements for krypton reported in the paper "Acoustic Isotherms for Nitrogen Argon and Krypton", by S. S. Lestz. The Journal of Chemical Physics, Volume 38, page 2830 (1963) shows that the speed of sound c in krypton gas follows the relationship $c = 224.25 - 0.164 P$ meters per second where P is the pressure in atmospheres. If the light beams 26 and 28 are one centimeter apart then at seven atmospheres of pressure the time period $t_2 - t_1 = 44823$ nsec. At P=6 atmospheres then $t_2 - t_1 = 44790$ nsec, a decrease of 33 nsec. Thus the arithmetic circuit 46, given the time period $t_2 - t_1$ can calculate the pressure of the krypton fill gas in the lamp. Alternatively, the arithmetic circuit may be replaced by a comparison circuit having stored therein two numbers representing the acceptable time period limits and an output indicating whether the measured time is within the acceptable range.

The speed of sound in gas is also a function of temperature. If the subject method is to yield accurate results the temperature of the lamps being tested must be held at a specified temperature or the measurement must be compensated for temperature variations.

It will thus be seen that this invention provides a method of measuring the pressure of a gas sealed in a lamp envelope to determine whether it is filled to an adequate pressure.

The embodiments of the invention in which an exclusive property or privilege is claimed are defined as follows:

1. The method of measuring the fill gas pressure in a light bulb having a transparent envelope, comprising the steps of:

> thermally generating a shock wave in the fill gas at a source within the bulb which wave travels from the source at the speed of sound in the gas, the speed of the shock wave depending on the fill gas pressure,
>
> optically detecting the passage of the shock wave through two loci in the bulb, one of the loci being further from the source than the other of the loci by a known distance so that the shock wave successively passes through the two loci,
>
> measuring the time of travel of the shock wave between the two loci, and
>
> determining from the known distance and the time of travel the fill gas pressure for the bulb.

2. The method of measuring the fill gas pressure in a light bulb having a transparent envelope, comprising the steps of:

> thermally generating a shock wave in the fill gas at a source within the bulb which wave travels from the source at the speed of sound in the gas, the speed of the shock wave depending on the fill gas pressure,
>
> passing two light beams through the bulb, one of the beams at a known distance further away from the source than the other beam so that the shock wave successively perturbs the light beams as it passes through them,
>
> optically detecting the passage of the shock wave through the two beams,
>
> measuring the time of travel of the shock wave between the two beams, and
>
> determining from the known distance and the time of travel the fill gas pressure for the bulb.

3. The method of measuring the fill gas pressure in a light bulb having a pair of filaments within a transparent envelope, comprising the steps of:

> thermally generating a shock wave in the fill gas by applying a voltage across the filaments to create an electrical arc which wave travels at the speed of sound in the gas, the speed of the shock wave depending on the fill gas pressure,
>
> optically detecting the passage of the shock wave through two loci in the bulb, one of the loci being further from the source than the other of the loci by a known distance so that the shock wave successively passes through the two loci,
>
> measuring the time of travel of the shock wave between the two loci, and
>
> determining from the known distance and the time of travel the fill gas pressure for the bulb.

* * * * *